United States Patent [19]

Erb

[11] Patent Number: 5,080,681
[45] Date of Patent: Jan. 14, 1992

[54] HAND WITH CONFORMABLE GRASP

[75] Inventor: Robert A. Erb, Valley Forge, Pa.

[73] Assignee: Calspan Corporation, Buffalo, N.Y.

[21] Appl. No.: 579,509

[22] Filed: Sep. 10, 1990

[51] Int. Cl.⁵ .............................................. A61F 2/54
[52] U.S. Cl. ........................................ 623/63; 294/902; 901/21
[58] Field of Search ................................ 623/63–65, 623/58, 24, 25; 901/21, 28, 25, 39; 414/1, 2, 7; 294/902

[56] References Cited

U.S. PATENT DOCUMENTS

| 2,497,493 | 2/1950 | Edwards . | |
| 2,641,769 | 6/1953 | Robinson . | |
| 2,696,010 | 12/1954 | Robinson . | |
| 3,694,021 | 9/1962 | Mullen | 294/106 |
| 4,466,800 | 8/1984 | Breiden | 623/64 X |
| 4,685,929 | 8/1987 | Monestier | 623/64 |
| 4,770,662 | 9/1988 | Giampapa | 623/24 |
| 4,834,761 | 5/1989 | Walters | 623/26 |

FOREIGN PATENT DOCUMENTS

| 0156340 | 4/1978 | Netherlands | 901/28 |
| 2171076 | 8/1986 | United Kingdom | 901/21 |
| 8404722 | 12/1984 | World Int. Prop. O. | 901/21 |

OTHER PUBLICATIONS

"Cosmetic Covers for Upper Extremity Prostheses", *Rehabilitation R & D Progress Reports 1987*, Veterans Administration, p. 37.

Primary Examiner—Randall L. Green
Assistant Examiner—David H. Willse
Attorney, Agent, or Firm—Biebel & French

[57] ABSTRACT

A mechanical hand comprising a housing with a first sliding actuation member and second sliding actuation member, at least two elongate, bendable members comprising a proximal phalanx and a distal phalanx, a relatively stationary member attached to the housing, a primary tension member projecting through the housing and at least through the second sliding actuation member, and a set of primary tendons and a set of secondary tendons. The primary tendons have first and second ends, with the primary tendon first end secured to the first slidable actuation member, and with the primary tendons extending through the bendable members. The primary tendon second end is secured to the distal phalanx. Each secondary tendon has first and second ends. The secondary tendon first end is secured to the second slidable actuation member. The secondary tendons extend through the bendable members. The secondary tendon second end is secured to the proximal phalanx. A method for having the mechanical hand of this invention exhibit a conformable grasp is also disclosed.

20 Claims, 4 Drawing Sheets

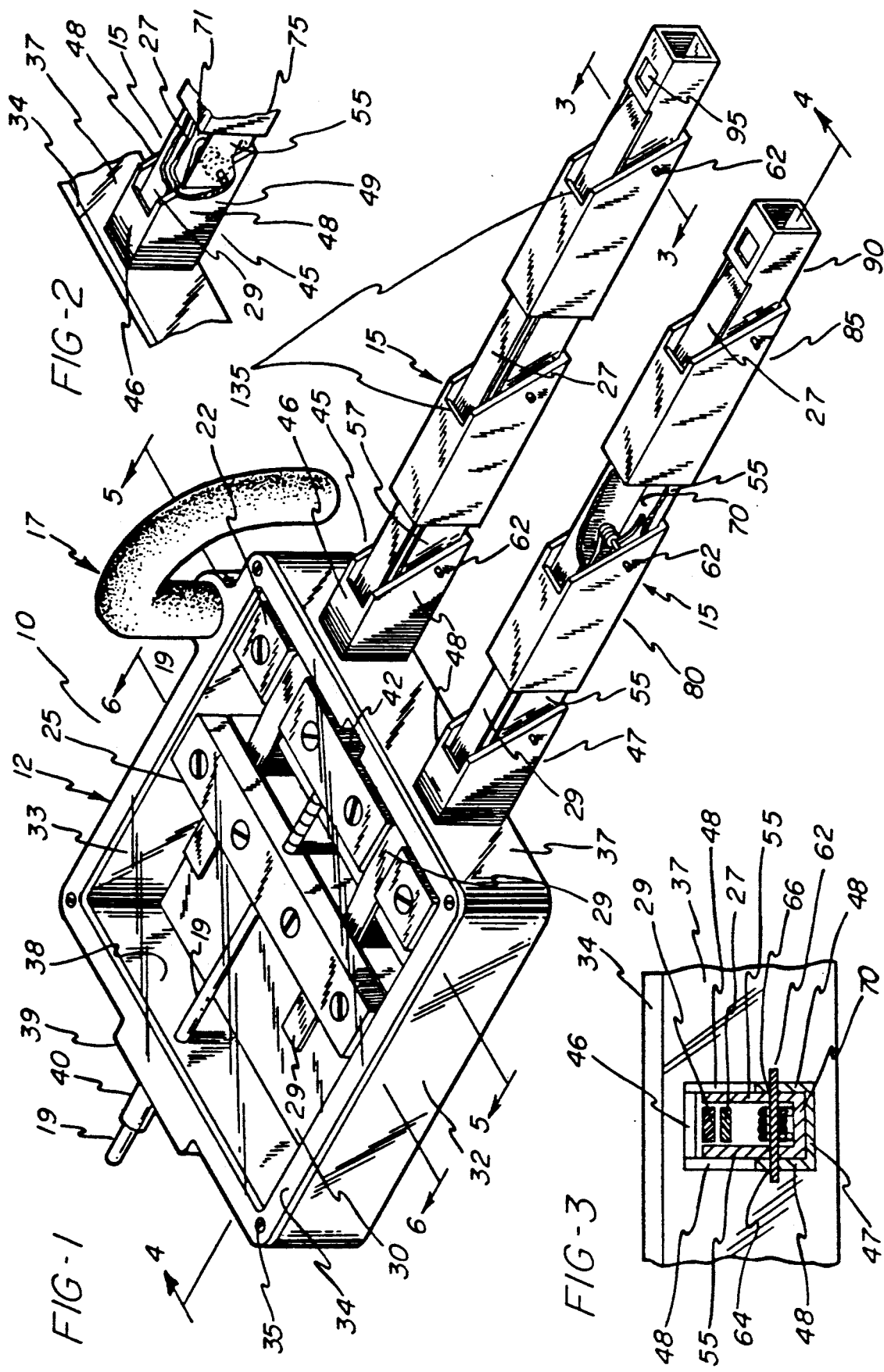

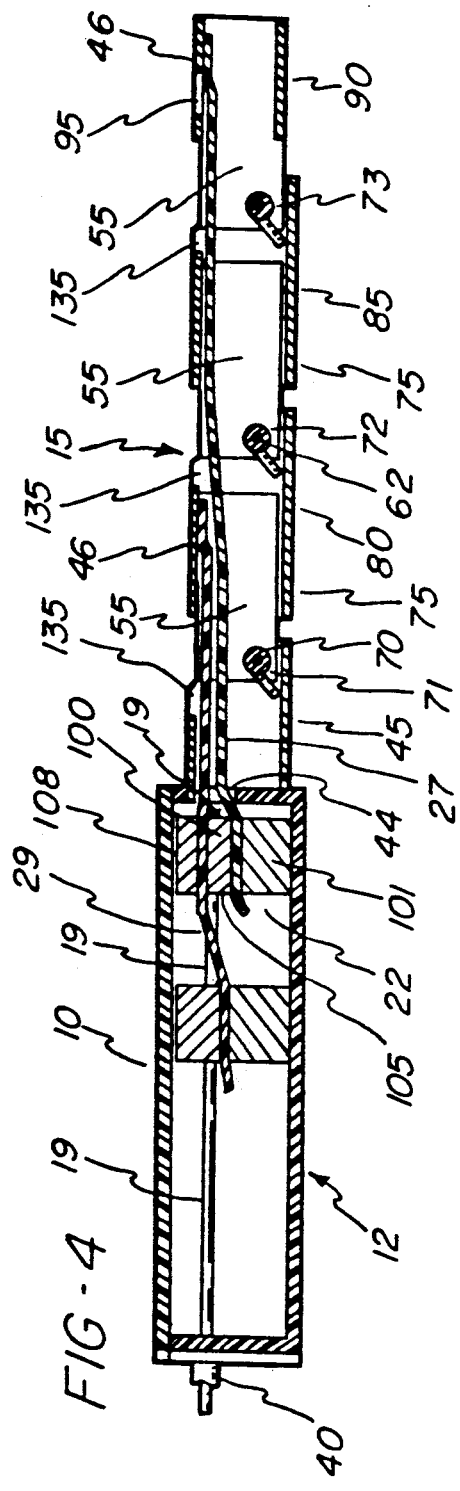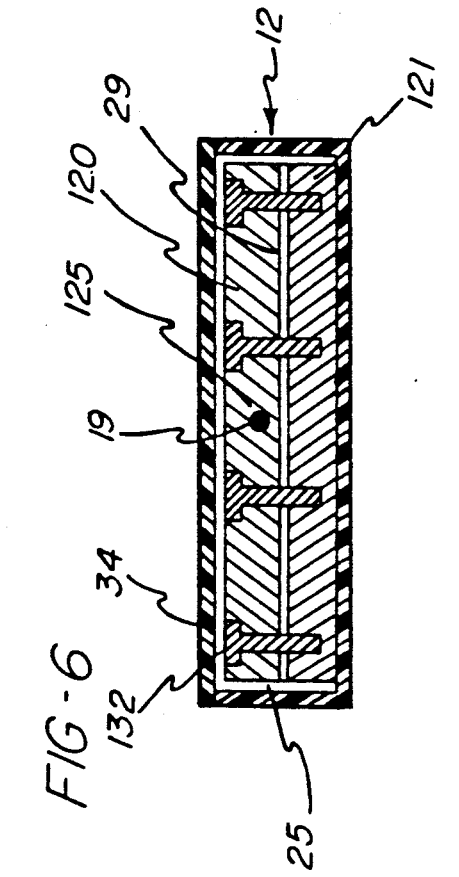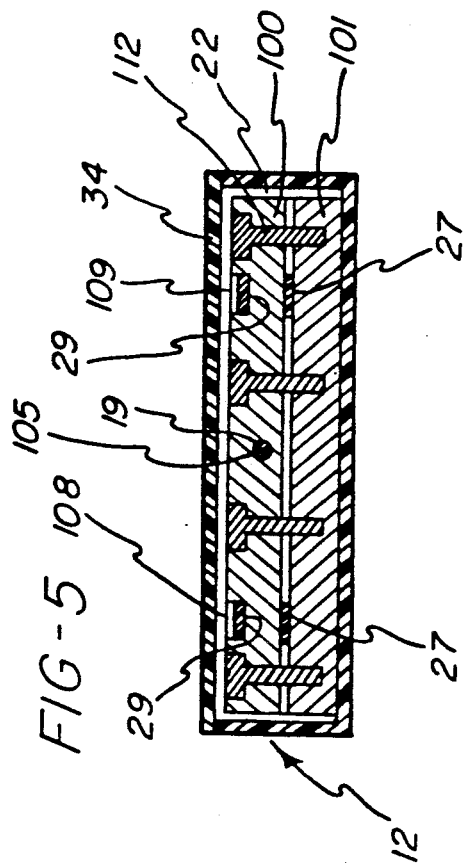

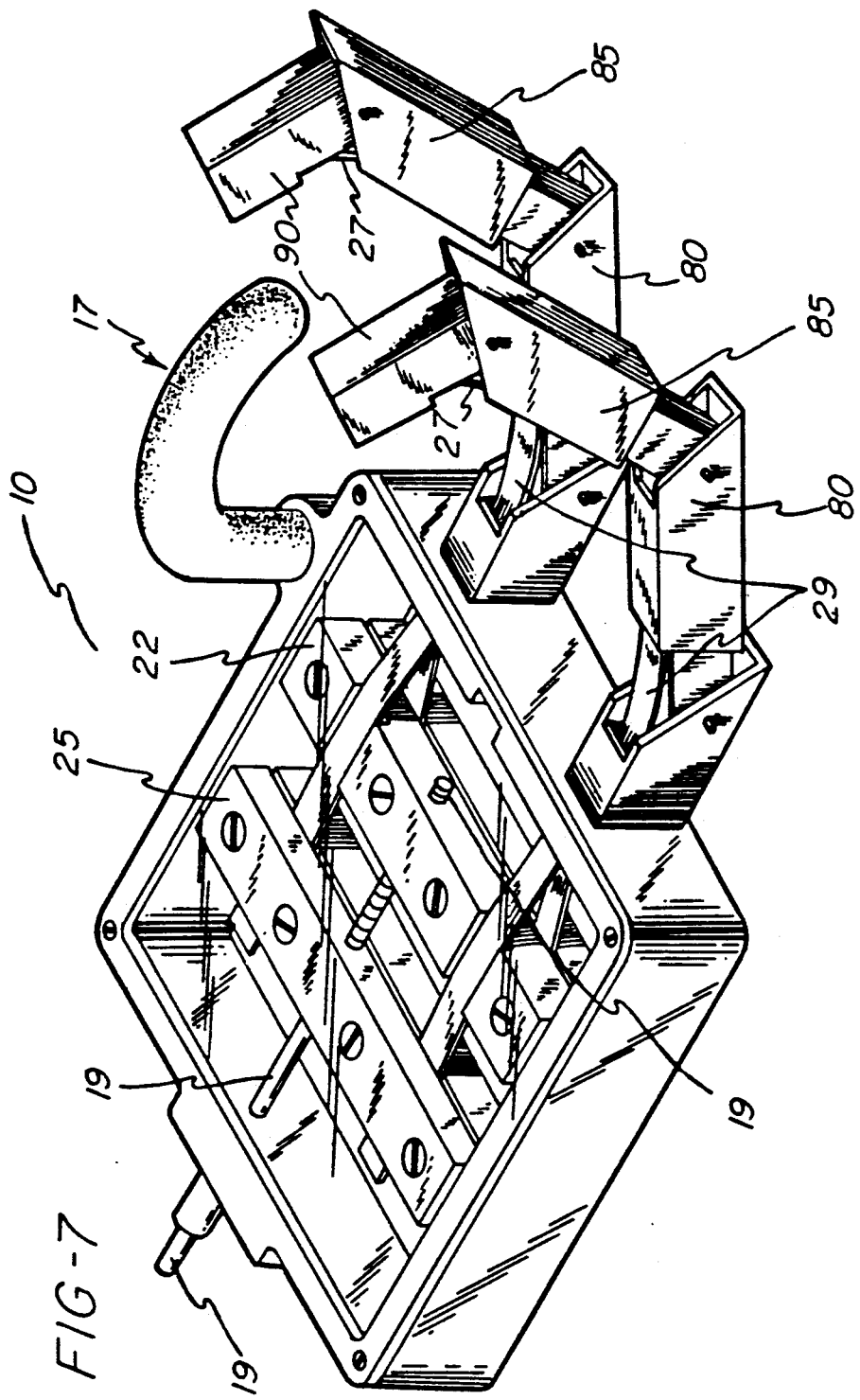

HAND WITH CONFORMABLE GRASP

BACKGROUND OF THE INVENTION

The present invention relates generally to a hand prosthesis and the like, and more particularly, to such a device as permits the hand to have a conformable grasp.

Many efforts have been made to construct a mechanical hand. Generally the mechanical hands heretofore known were specifically designed for use by amputees, although some have been designed for use in robotics, for example as end effectors. Initially, the amount of useful work which such artificial hands were capable of performing was seriously limited by their relative lack of strength. This problem was coupled with the fact that many artificial hands were incapable of producing independent finger movements necessary to duplicate the complex movements of a human hand.

Over the years, prosthetic hands have been developed with adequate strength components thereby enabling the hand to function in tasks where strength is important, for example, in holding open a door, or pulling up or down on a handle such as in carrying luggage or in closing an overhead garage door. Attempts at providing mechanical hands with sufficient dexterity to, for example, hold a pencil, hold a flower stem, turn the pages of a book, or grasp a needle resulted in a quite complicated mechanical hand, of the type which was subject to frequent repair and which was prohibitively expensive for most people.

It is thus apparent that the need exists for an improved mechanical hand which provides the dexterity required for many applications, yet at the same time being dependable and relatively inexpensive.

SUMMARY OF THE INVENTION

The problems associated with prior art mechanical hands are overcome in accordance with the present invention by a hand with conformable grasp comprising a housing with two slidable actuation members contained therein, which slidable members are secured to strips which function as tendons. A pair of tendons secured to the first and second actuation members have their opposite ends longitudinally disposed within telescoping rectangular metal tubing which function similar to fingers. Each of the finger-like bendable members comprise a plurality of phalanxes which correspond to the digits of a human finger. Additionally, each phalanx bends relative to the ones adjacent to it as the tendons are slidably moved through the phalanxes such that the area where pivoting occurs approximates knuckles.

At each knuckle area, a spring assists in providing extension of the finger elements. The springs associated with this invention preferably are torsion springs and although they may all be of the same spring constant, the utilization of springs with unequal spring constants permits the hand to exhibit even more life-like movement. Also located in this knuckle region are means for preventing hyperextension of each of the respective fingers in the knuckle area.

Preferably the hand of this invention utilizes at least two bendable members which in conjunction with a stationary member permit the establishment of a plane with respect to the object to be grasped. This stationary member functions similarly to a thumb and may be of a malleable substance or just simply a pivotable rod.

There is also disclosed in this invention a method for having a mechanical hand exhibit a conformable grasp comprising the steps of displacing a rod which functions as a tension member along a prescribed path. During the displacement, the rod projects completely through one and at least partly through the other actuation member. The displacement of the primary tension member displaces both sliding actuation members and causes them to move longitudinally away from the fingers.

As the actuation members move away from the fingers, they pull with them the tendon members. The bending of the fingers is in response to the shortening of the length of the tendons within each bendable member as the result of the displacement of the actuation members in the housing. This method causes the distal phalanxes to be brought towards the relatively stationary thumb member.

It is the primary object of the present invention to provide a hand with a conformable grasp which is relatively simple to fabricate, efficient, and relatively inexpensive.

Another object of the invention is to provide a mechanical hand having finger digits formed of connecting segments, jointed to include limits of flexibility that prohibit the reverse flexing of the respective digits beyond that capable in a human hand, to provide an aesthetically pleasing prosthesis.

Still another object of the present invention is to provide a mechanical hand whose dimensions can be altered to match hands or prosthetic covers of various sizes.

Still another object of the present invention is to provide an artificial hand which can grip a variety of objects and yet not lose its grip.

Other objects and advantages of the invention will be apparent from the following description, the accompanying drawings and the appended claims.

BRIEF DESCRIPTION OF THE DRAWINGS

FIG. 1 is a perspective view of a hand prosthesis in accordance with the present invention without the hand being encased in a glove.

FIG. 2 is an exploded perspective view on a greatly enlarged scale showing the area of an elongate member associated with the basal phalanx.

FIG. 3 is a vertical sectional view on a greatly enlarged scale taken along line 3—3 of FIG. 1.

FIG. 4 is a vertical sectional view on a greatly enlarged scale taken along line 4—4 of FIG. 1.

FIG. 5 is a vertical sectional view on a greatly enlarged scale taken along line 5—5 of FIG. 1.

FIG. 6 is a vertical sectional view on a greatly enlarged scale taken along line 6—6 of FIG. 1.

FIG. 7 is a perspective view similar to FIG. 1 but showing the bendable members in a flexed position.

DETAILED DESCRIPTION OF THE INVENTION

Figure 8:
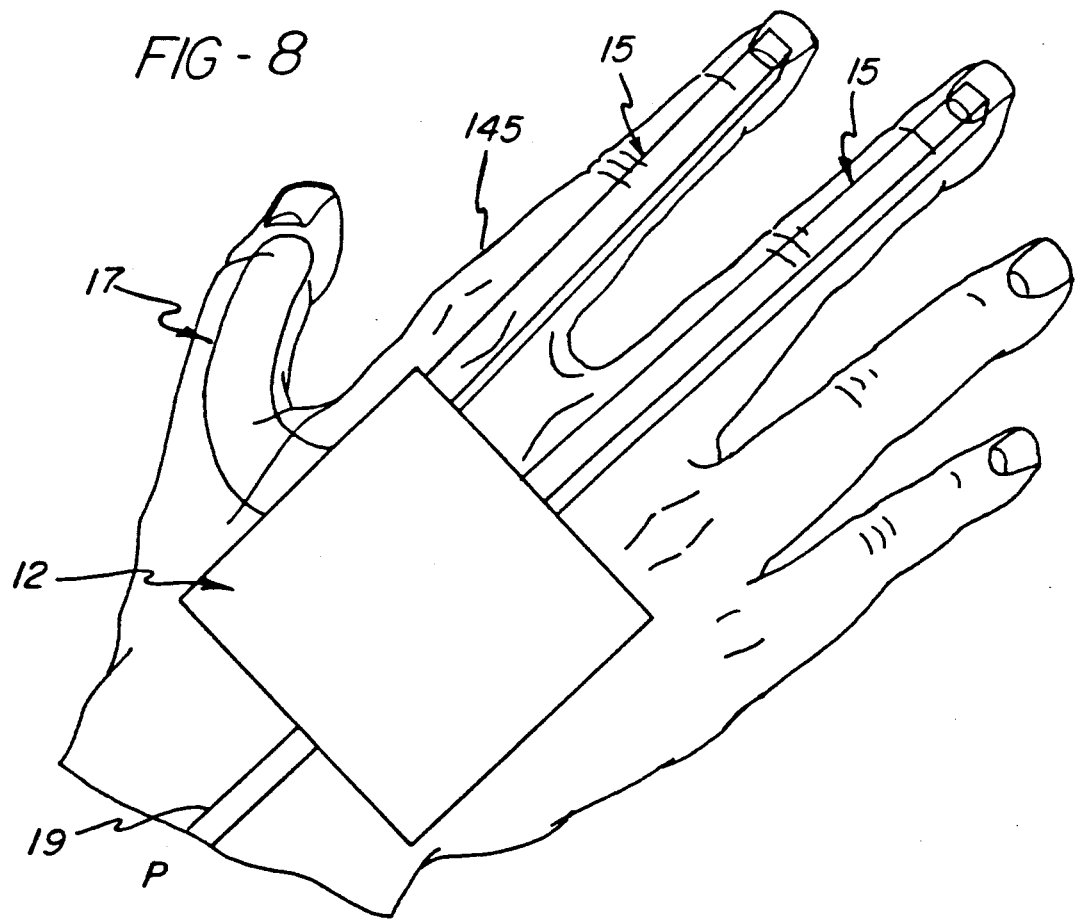
FIG. 8 is a schematic view showing the invention encased in a cover.

Having reference to the drawings, attention is directed first to FIG. 1 which discloses a perspective view of a hand with conformable grasp made in accordance with the teachings of the present invention, but without having the device encased within a glove, with the mechanical hand being designated generally by the numeral 10. Hand 10 is comprised of a housing 12, at least two elongate bendable members 15 and a relatively stationary member 17.

The housing is shown as being a roughly rectangular structure which could be fabricated from metal or even a plastic. The elongate bendable members 15 are shown as being at least two in number, but could range up to four. They are shown as being approximately the same length, but could be fabricated in different lengths to more closely approximate the various relative lengths of human fingers. The relatively stationary member 17 is shown as a malleable rod which could be bent to approximate the shape of a flexed thumb. Alternatively, the stationary member could be fabricated using at least one ball joint in conjunction with inflexible rods.

The source of tension for this invention is provided by a primary tension member 19 in the form of a wire rod which extends from outside the housing, through the wall of the housing, and across the interior of the housing passing through a first sliding actuation member 22 as well as a second sliding actuation member 25. As can be seen in FIGS. 1-4, anchored to first sliding actuation member 22 and extending through the interior of the elongate bendable members 15 is a primary tendon 27. Similarly, anchored to the second sliding actuation member 25 and extending over first sliding actuation member 22 and primary tendon 27 through a portion of the elongate bendable member 15 is a secondary tendon 29. Preferably both the primary and secondary tendons 27 and 29 respectively are fabricated from a flexible as well as strong substance, such as strips of polyester.

The housing 12 of hand 1-0 comprises a base 30 and a pair of opposing side walls 32 and 33 respectively. Preferably the housing 12 also includes a planar cover 34 secured to the housing by cover attachment means 35, such as screws or other appropriate fastening means. The housing 12 also includes a housing front wall 37 adjacent the elongate bendable members 15, and a rear wall 38. The rear wall has a thicker wall portion in the area surrounding the passage therethrough of primary tension member 19. Rod 40, which serves as a conduit for tension member 19, is preferably secured to the housing 12 in the area of the thicker wall portion 39.

Additionally, the housing front wall 37 comprises a front wall groove 42 which extends from the top to the bottom of that particular wall and only part way through the wall from the interior of the housing. The front wall 42 is oriented along the same axis as primary tension member 19, such that any projection of the end of tension member 19 through first sliding actuation member 22 terminates within the front wall groove. Additionally, a plurality of front wall apertures 44 exist in the housing front wall 37 to permit primary and secondary tendons 27 and 29 respectively to pass through the front wall and thence into the interior of the elongate bendable members 15.

As can be seen in FIGS. 1-4, a basal phalanx exists directly adjacent to the housing front wall 37 and is the first phalanx associated with the elongate bendable members 15. Each phalanx associated with elongate bendable members 15 comprises a phalanx top 46, a phalanx bottom 47, phalanx side walls 48 and a beveled or angled portion 49. The presence of a solid, supporting region in phalanx bottom 47 in the region of angled portion 49 beneath each of the respective springs in each phalanx serves as means to preclude or prevent hyperextension of the finger elements.

A phalanx connector 55 having a phalanx connector proximal end 57 and a phalanx connector distal end 59 serves as a means for joining adjacent phalanx members. The phalanx connector extends to most of the height of the phalanxes, and assists in maintaining alignment and stability between the inner 55 and the outer tubing 48. The phalanx connector proximal end telescopes within the side walls of the preceding phalanx and is retained in pivotal relationship thereto by joint pin 62 which passes through a phalanx side wall aperture 64 in the opposing side walls 48 of each phalanx as well as through phalanx connector aperture 66 in each side wall of the phalanx connector proximal end 57. The bottom end wall of each phalanx connector, which wall is closest to the housing, is slightly rounded as shown in FIG. 4. This rounded portion avoids interference between the phalanx members and connectors during flexure.

The joint pin 62 passes through a spring 70 which, in the embodiment of the hand shown, includes a first spring 71, second spring 72 and a third spring 73. Although various types of springs could be used, preferably the hand has incorporated therein torsion springs. It has been found that torsion springs provide extension better than other spring means. The presence of these torsion springs in each finger joint provides extension of the fingers as well as resistance to the action of the primary and secondary tendons.

Adjacent basal phalanx 45 is proximal phalanx 80. The configuration of proximal phalanx 80 can be seen as being approximately the same as that of basal phalanx 45. A medial phalanx 85 preferably is provided. The medial phalanx is also of the same general shape as the proximal phalanx. Finally, a distal phalanx 90 is shown. The configuration of the distal phalanx varies slightly from the configuration of the other phalanxes. In fact, the distal phalanx more closely resembles phalanx connectors 55 due to the presence of a joint pin through the proximal end of the distal phalanx. Although this particular phalanx also include a phalanx top 46, a phalanx bottom 47 and phalanx side walls 48 it does not include a beveled or angled portion 49. Instead it includes a distal phalanx aperture 95 in its phalanx top.

It would be appreciated especially by reference to FIG. 4 that the primary tendon 27 extends through the basal phalanx, the proximal phalanx, the medial phalanx and terminates in the region of the distal phalanx 90 with its being secured to the phalanx top 46. As disclosed, the point of attachment is preferably located between the distal phalanx aperture 95 and the tip of the distal phalanx. Meanwhile, secondary tendon 29 extends into the elongate bendable member 15 through the basal phalanx and into the region of the proximal phalanx where the secondary tendon 29 is secured to the phalanx top of the proximal phalanx 80.

Turning now to FIGS. 5 and 6, the first sliding actuation member 22 is shown as comprising a first sliding actuation member part 100 and a first sliding actuation member part 101, both of which are relatively rectangular in shape and positioned in superposed relationship to one another. A first sliding actuation member aperture 105 is shown as extending through actuation member first part 100 and serves as a passage for primary tension member 19.

First sliding actuation member 22 also includes a first groove 108 and a second groove 109 preferably parallel to one another. These grooves are in the top surface of the first sliding actuation member first part 100 and are slightly greater in width than the width of the primary and secondary tendons 27 and 29. As can be seen in FIG. 5, these grooves serve as a channel through which the secondary tendons 29 slide. The first sliding actuation member first part and second part are secured to one another by fastening means 112 which preferably are recessed into the top of the first sliding actuation member first part.

Second sliding actuation member 25 can be seen as comprising a first part 120 and a second part 121. As with the first sliding actuation member 22, the second sliding actuation member has an aperture 125 passing therethrough along the same axis as first sliding actuation member aperture 105. Additionally, fastening means 132 secure the respective first and second parts of the second sliding actuation member together similar to fastening means 112.

Primary tendons 27 are held in secured relationship between first sliding actuation member first part and second part as can be seen in FIG. 5. Similarly, secondary tendons 29 are held in secured relationship between second sliding actuation member first part and second part 120 and 121 respectively. Both first and second sliding actuation members are preferably fabricated from plastic or of metal.

Actual operation of this mechanical hand having a conformable grasp can be appreciated by a comparison of FIGS. 1, 4, and 7. By displacing the primary tension member 19 along a prescribed path through the conduit 40 and housing 12, the first sliding actuation member to which it is fixedly secured is pulled toward rear wall 38. When the first sliding actuation member contacts second sliding actuation member 25, the second sliding actuation member is also displaced towards rear wall 38. It should be remembered that the tension member 19 merely passes through the aperture 125 of second sliding actuation member 25, and is not secured thereto.

The displacement of the first and second actuation members 22 and 25 towards rear wall 38 causes the displacement of primary and secondary tendons 27 and 29 as well. It should be remembered that initially only the primary tendon 27 is displaced until such time as the first sliding actuation member 22 makes contact with second sliding actuation member 25. At that time, secondary tendon member 29 is also displaced. The displacement of the two tendons through tubular members 15 causes the effectual bending of the elongate members in response to the shortening of the length of the primary and secondary tendons within them.

In response to the displacement of primary tendon 27, the distal phalanx bends towards the rest of the hand. Eventually, the medial phalanx bends too. In response to the displacement of secondary tendon 29, the proximal phalanx bends towards the rest of the hand. This bending also causes the displacement of the medial and distal phalanxes towards the stationary member. Consequently, the distal phalanx is brought towards the relatively stationary member 17. As the finger members bend toward the stationary member 17 the presence of recessed phalanx portions 135 in the basal, proximal and medial phalanxes permits the phalanx connectors and distal phalanx to bend more than 90° with respect to the elongate axis associated with the bendable members in their rest position as shown in FIG. 1.

In actual operation, the tension member 19 could be driven by various power sources P. For example, when the hand is used as a prosthesis, the tension member could be driven by a cable actuated by a shoulder harness in the manner utilized in known prosthetic devices. Alternatively, the prosthesis could involve a myoelectric hand using muscle signals, whereby a rotational motor pulls on the cable. A third possibility would be to utilize a myoelectric hand whereby the muscle signals would activate a linear motor or solenoid.

Furthermore, the telescopic tubing of this invention ma have the lengths of the various phalanxes slidably adjusted prior to attachment relative to one another by pins 66 in order to more closely match the dimensions of a hand or prosthetic cover. Alternatively, the various phalanxes may be different lengths to approximate variant digit size. Thus, the hand size may be adjustable. This is a significant departure from the prior art, wherein the phalanxes for hands or robotic end effectors or the hands themselves, were of a fixed size to which a glove was adjustably secured. With the hands of this invention, the hand may be in effect custom-made to fit any size glove, thereby resulting in a more life-like hand in the case of a prosthesis. Additionally, the torsion spring at different joints could have the same or unequal spring constant, depending in part upon how the hand is to be used. Also, the use of springs with unequal spring constants permits digits to move at different applications of force, thereby resulting in a more natural movement.

As can be seen in FIG. 8, a glove 145 is fabricated for use as covering for the hand 10. Preferably the glove would include a knitted KEVLAR ® sleeve placed between the hand and a typical prosthetic cover. An alternative to the knitted KEVLAR ® sleeve would be the use of a soft deformable layer such as foam. Over the knitted KEVLAR ® sleeve or soft deformable layer preferably is placed a silicone or vinyl glove 145.

Prior to covering the hand 10 with the glove, the gripping tension may be adjusted with respect to the point of securing tension member 19 to first sliding actuation member 22. The more of tension member 19 which passes through the first sliding actuation member 22, the greater the relative gripping force when tension member 19 is actually displaced. The adjustment of the tension permits this hand to be more dexterous than most prior art prosthetic hands. Additionally, it permits the hand to be more conformable with respect to objects which it grasps.

While the form of apparatus and method herein described constitutes a preferred embodiment of this invention, it is to be understood that the invention is not limited to this precise form of apparatus and method and that changes may be made therein without departing from the scope of the invention, which is defined in the appended claims.

What is claimed is:

1. A method for having a mechanical hand exhibit a conformable grasp comprising the steps of displacing a primary tension member along a prescribed path, said tension member projecting through a housing, said housing comprising a first sliding actuation member and a second sliding actuation member, said tension member projecting at least through said second sliding actuation member, said housing having a relatively stationary member attached thereto, said housing having at least two elongate, bendable members attached thereto, said bendable members comprising a proximal phalanx and a distal phalanx, said displacement of said primary tension member being away from the attachment of said housing to said bendable members, said displacement of said primary tension member displacing said first sliding actuation member and said second sliding actuation member, displacing said first sliding actuation member and said second sliding actuation member away from the attachment of said housing to said bendable members, said first sliding actuation member having attached thereto a first end of at least two primary tendons, the second sliding actuation member having attached thereto a first end of at least two secondary tendons, each of said bendable members having extending therethrough a primary tendon with a primary tendon second end secured to said distal phalanx, each of said bendable members having extending therethrough a secondary tendon with a secondary tendon second end secured to said proximal phalanx, and bending said bendable members in response to the shortening of the length of said primary and secondary tendons within said bendable members as a result of the displacement of said first and second sliding actuation members.

2. The method of claim 1 in which the distal phalanxes are brought towards said relatively stationary member.

3. A hand with conformable grasp comprising a housing, said housing comprising a first sliding actuation member and a second sliding actuation member, at least two elongate, bendable members, said bendable members comprising a proximal phalanx and a distal phalanx, said bendable members comprising telescoping components, a relatively stationary member, said relatively stationary member attached to said housing, a primary tension member, said tension member projecting through said housing and at least through said second sliding actuation member, said first sliding actuation member having secured thereto said primary tension member, and a set of primary tendons and a set of secondary tendons, each primary tendon having first and second ends, said primary tendon first end secured to said first sliding actuation member, said primary tendons extending through said bendable members, said primary tendon second end secured to said distal phalanx, each secondary tendon having first and second ends, said secondary tendon first end secured to said second sliding actuation member, said secondary tendons extending through said bendable members, said secondary tendon second end secured to said proximal phalanx, said first sliding actuation member comprising a first part and a second part, said first part having first and second grooves formed therein, said primary tendon secured between said first sliding actuation member first part and second part.

4. The hand according to claim 3 wherein said phalanxes are of different lengths to provide for adjustable hand size.

5. The hand according to claim 3 wherein said bendable members include means for providing extension.

6. The hand according to claim 3 wherein said housing includes a front wall, a rear wall, a pair of side walls, a base and a cover.

7. The hand according to claim 3 wherein said second sliding actuation member comprises a first part and a second part, said secondary tendon secured between said second sliding actuation member first part and second part.

8. The hand according to claim 3 wherein said bendable members each include a basal phalanx.

9. The hand according to claim 8 wherein said bendable members each include a medial phalanx.

10. The hand according to claim 3 wherein said hand is encased in a glove.

11. The hand according to claim 3 wherein said housing has at least two of said bendable members attached thereto, and wherein said primary tension member and said first sliding actuation member are displaced away from the attachment of said bendable members to said housing.

12. A hand with conformable grasp comprising a housing, said housing comprising a front wall, a rear wall, a pair o side walls, a base, a cover, a first sliding actuation member and a second sliding actuation member, wherein said front wall includes a front wall groove and at least two front wall apertures, and said first sliding actuation member having first and second grooves, at least two elongate, bendable members, said bendable members comprising a proximal phalanx and a distal phalanx, said bendable members comprising telescoping components, a relatively stationary member, said relatively stationary member attached to said housing, a primary tension member, said tension member projecting through said housing and at least through said second sliding actuation member, said first sliding actuation member having secured thereto said primary tension member, and a set of primary tendons and a set of secondary tendons, each primary tendon having first and second ends, said primary tendon first end secured to said first sliding actuation member, said primary tendons extending through said bendable members, said primary tendon second end secured to said distal phalanx, each secondary tendon having first and second ends, said secondary tendon first end secured to said second sliding actuation member, said secondary tendons extending through said bendable members, said secondary tendon second end secured to said proximal phalanx.

13. The hand according to claim 12 which includes each of said first and second grooves being aligned with one of said bendable members and said front wall apertures.

14. The hand according to claim 12 wherein said primary tension member is aligned with said front wall groove.

15. A hand with conformable grasp comprising a housing, said housing comprising a first sliding actuation member and a second sliding actuation member, at least two elongate, bendable members, said bendable members comprising a proximal phalanx and a distal phalanx, said bendable members comprising telescoping components, said bendable members including torsion springs, a relatively stationary member, said relatively stationary member attached to said housing, a primary tension member, said tension member projecting through said housing and at least through said second sliding actuation member, said first sliding actuation member having secured thereto said primary tension member, and a set of primary tendons and a set of secondary tendons, each primary tendon having first and second ends, said primary tendon first end secured to said first sliding actuation member, said primary tendons extending through said bendable members, said primary tendon second end secured to said distal phalanx, each secondary tendon having first and second ends, said secondary tendon first end secured to said second sliding actuation member, said secondary tendons extending through said bendable members, said secondary tendon second end secured to said proximal phalanx.

16. The hand according to claim 15 wherein torsion springs at different joints have unequal spring constants.

17. A hand with conformable gras comprising a housing, said housing comprising a first sliding actuation member and a second sliding actuation member, at least two elongate, bendable members, said bendable members comprising a proximal phalanx and a distal phalanx, said bendable members comprising telescoping components, said bendable members including means for preventing hyperextension, a relatively stationary member, said relatively stationary member attached to said housing, a primary tension member, said tension member projecting through said housing and at least through said second sliding actuation member, said first sliding actuation member having secured thereto said primary tension member, and a set of primary tendons and a set of secondary tendons, each primary tendon having first and second ends, said primary tendon first end secured to said first sliding actuation member, said primary tendons extending through said bendable members, said primary tendon second end secured to said distal phalanx, each secondary tendon having first and second ends, said secondary tendon first end secured to said second sliding actuation member, said secondary tendon second end secured to said proximal phalanx.

18. A mechanical hand comprising a housing, said housing comprising a front wall, a rear wall, a pair of side walls, a base, a cover, a first sliding actuation member and a second sliding actuation member, said first sliding actuation member having secured thereto a primary tension member, said front wall including a front wall groove and at least two front wall apertures, said first sliding actuation member having first and second grooves, at least two elongate, bendable members, said bendable members comprising telescoping components comprising a proximal phalanx and a distal phalanx, said bendable members including means for connecting said telescoping components, a relatively stationary member, said relatively stationary member attached to said housing, a primary tension member, said tension member projecting through said housing and at least through said second sliding actuation member, and a set of primary tendons and a set of secondary tendons, each primary tendon having first and second ends, said primary tendon first end secured to said first sliding actuation member, said primary tendons extending through said bendable members, said primary tendon second end secured to said distal phalanx, each secondary tendon having first and second ends, said secondary tendon first end secured to said second sliding actuation member, said secondary tendons extending through said bendable members, said secondary tendon second end secured to said proximal phalanx, said prosthesis encased in a glove.

19. A mechanical hand comprising a housing, said housing comprising a first sliding actuation member and a second sliding actuation member, said first sliding actuation member having secured thereto a primary tension member, at least two elongate, bendable members, said bendable members comprising telescoping components comprising a proximal phalanx and a distal phalanx, said bendable members including means for connecting said telescoping components, a relatively stationary member, said relatively stationary member attached to said housing, said primary tension member projecting through said housing and at least through said second sliding actuation member, and a set of primary tendons and a set of secondary tendons, each primary tendon having first and second ends, said primary tendon first end secured to said first sliding actuation member, said primary tendons extending through said bendable members, said primary tendon second end secured to said distal phalanx, each secondary tendon having first and second ends, said secondary tendon first end secured to said second sliding actuation member, said secondary tendons extending through said bendable members, said secondary tendon second end secured to said proximal phalanx, said prosthesis encased in a glove, said first sliding actuation member comprising a first part and a second part, said first part having first and second grooves formed therein, said primary tendon secured between said first sliding actuation member first part and second part.

20. The hand according to claim 19 wherein said second sliding actuation member comprises a first part and a second part, said secondary tendon secured between said second sliding actuation member first part and second part.

* * * * *